United States Patent [19]

Au

[11] Patent Number: 4,605,737
[45] Date of Patent: Aug. 12, 1986

[54] ACYL DERIVATIVES OF TRIS-HYDROXY-ETHYL-PERHYDRO-1,3,5-TRIAZINE

[75] Inventor: Andrew T. Au, Needham, Mass.

[73] Assignee: The Dow Chemical Company, Midland, Mich.

[21] Appl. No.: 602,779

[22] Filed: Apr. 23, 1984

[51] Int. Cl.$^4$ .................................... C07D 251/04
[52] U.S. Cl. ............................................. 544/215
[58] Field of Search ................................. 544/215

[56] References Cited

PUBLICATIONS

Hawley, *Condensed Chemical Dictionary*, 10th Ed., Van Nostrand Reinhold Co. New York, N.Y. 1981 pp. 450, 460.

Morrison and Boyd, *Organic Chemistry*, 3rd Ed., Allyn and Bacon, Inc. Boston, MA (1973) p. 556.

*Primary Examiner*—Richard A. Schwartz
*Assistant Examiner*—J. G. Mullins
*Attorney, Agent, or Firm*—Douglas N. Deline; Michael S. Jenkins; Christopher John Rudy

[57] ABSTRACT

Fatty acid ester derivatives of 1,3,5-tris(2-hydroxyalkyl)perhydro-s-triazine or mixed ester/ether derivatives thereof are corrosion inhibitors for acid-containing fluids. The compounds are also useful as emulsifiers, lubricants and hydraulic fluids.

5 Claims, No Drawings

ACYL DERIVATIVES OF TRIS-HYDROXY-ETHYL-PERHYDRO-1,3,5-TRIAZINE

BACKGROUND OF THE INVENTION

This invention relates to new compositions of matter and more particularly with improved compositions and processes for inhibiting corrosion of metals.

It is generally recognized that oil-producing formations often yield brine with the crude oil. This brine may be extremely corrosive in its action upon the oil-producing and collecting equipment, including the metal tubing, casings, pumps, pipe lines, and storage equipment. This type of corrosion is particularly noticeable in wells producing brine which contain varying amounts of hydrogen sulfide, carbon dioxide and other acidic materials therein.

Considerable effort has been directed in the past to reducing the cost of maintaining production and collection equipment free of corrosion by introducing into the well various corrosion inhibitors including formaldehyde, nitrogen bases of various types, amines, and combinations of the foregoing compounds.

In U.S. Pat. Nos. 3,819,527 and 2,889,277, certain tri(aryl)perhydro-s-triazine compounds are disclosed for use as corrosion inhibitors in aqueous systems such as crude oil streams or acid pickling baths.

In CA 87:105567q, 1,3,5-tris(2-hydroxyethyl)triazine is disclosed to be a suitable additive to sheet metal rolling lubricants to inhibit microbial growth which induces metal corrosion.

Ester derivatives of perhydro-s-triazine are known. In J. A. Bell et al., *J. Chem. Soc. c* 11, 1556-8 (1969), there is disclosed the compound 1,3,5-triazine-1-(2H)-methanol, tetrahydro-3,5-dinitro-, acetate corresponding to the formula:

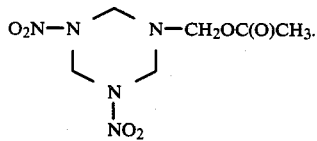

Also known are 1,3,5-tris(2-hydroxyethyl)perhydro-s-triazines disclosed and claimed in U.S. Pat. No. 4,266,054. The compounds were found to be useful solubilizing agents.

SUMMARY OF THE INVENTION

According to the present invention, there are provided novel ester derivatives of tris-hydroxyalkyl perhydro-s-triazines corresponding to the formula:

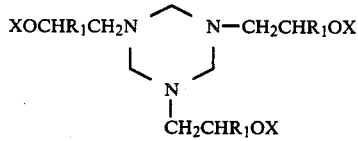

wherein $R_1$ is hydrogen, methyl or ethyl; and

X is hydrogen, $-CH_2CHR_1O)_nR$ or $-C(O)R$ where n is a number from zero to about 4, and R is alkyl, cycloalkyl, alkenyl or aryl of up to about 30 carbons, provided that in at least one occurrence, X is $-C(O)R$.

The compounds have been found to be effective corrosion inhibitors for iron-containing metals, especially steel in contact with acid-containing solutions including cleaning solutions used to clean or rid metallic surfaces of oxide scale or other undesired deposits and acidic solutions, such as oil or brine solutions that contact metal during pumping or other transfer process.

DETAILED DESCRIPTION OF THE INVENTION

The present invented compounds containing ester functionality are prepared by reaction of the corresponding tris-hydroxyalkyl perhydro-s-triazines and a carboxylic acid or a halide, ester or anhydride derivative thereof under appropriate reaction conditions for the esterification or ester interchange process. For example, the ester interchange is preferably conducted under conditions of high vacuum accompanied by the use of a phase-transfer catalyst. A preferred process for preparing esters involves the reaction of a carboxylic acid chloride with the tris-hydroxyalkyl perhydro-s-triazine in the presence of potassium carbonate.

Preferred carboxylic acid derivatives for preparation of esters of the present invention are fatty acids, either saturated or unsaturated having $C_{4-30}$ carbons. Examples include lauric, nonoic, sebacic, palmitic, stearic, oleic, linoleic and linolenic acids or mixtures thereof.

Ether functionality may be added at those hydroxyalkyl positions that are chosen to be unesterified by standard Williamson synthesis or by the techniques of U.S. Pat. No. 4,266,054, either before or after esterification.

The compounds of the invention are additionally employed as emulsifiers, lubricants and hydraulic fluids or as additives thereto. The preferred use is as a corrosion inhibitor. It is believed without wishing to be bound thereby that the corrosion inhibiting properties of the present compounds are due to the formation upon decomposition in situ to thereby generate formaldehyde and amine functionality.

When in use in a producing oil field, the compositions in a carrier such as an alcohol, kerosene or crude oil, may be injected under pressure into the oil field. Thereafter due to the hydrophobic nature of the ester functionality, the compounds of the invention are incorporated and dispersed into the crude oil present in the producing oil formation. After treatment of a producing oil field is finished, the crude oil containing the corrosion inhibitor may be removed by normal techniques. In an alternate procedure, the invented corrosion inhibitors may be added to the crude oil in small quantities as the oil is pumped, as for example, by injection at the bottom of an oil well casing or at any other convenient point during the pumping process.

When employed in a pickling bath or other corrosive environment, the present invented compounds are merely added to the corrosive fluid in use.

While any amount effective to prevent corrosion may be employed, preferred are amounts from about 0.001 percent to 10 percent by weight based on the weight of crude oil, pickling bath or other fluid being protected. Preferred are amounts from about 0.1 percent to about 1 percent.

SPECIFIC EMBODIMENTS

Having described the invention, the following examples are provided as further illustrative of the present compositions and are not to be construed as limiting.

EXAMPLE 1

1,3,5-Triazine-1,3,5(2H, 4H, 6H)triethanol Monooleate 1,3,5-Tris(2-hydroxyethyl)perhydro-s-tria-zine (21.6 g, 0.1 mole) and potassium carbonate (35 g) are combined in a mixture of 50 ml of water and 150 ml of methylene chloride at 0° C. Oleic acid chloride (30 g, 0.1 mole) in 50 ml of methylene chloride is added at a rate such that the reaction mixture is retained at a temperature below about 10° C. After complete addition, the mixture is stirred at 0° C. for 15 hours and then at about 25° C. for an additional 16 hours. The organic layer is separated, dried over magnesium sulfate and concentrated to a yellow oil. Analysis by infrared spectroscopy and nuclear magnetic resonance spectroscopy identify the product as 1,3,5-triazine-1,3,5-(2H, 4H, 6H)triethanol monooleate.

EXAMPLE 2

Di- and Triester

The reaction conditions of Example 1 are substantially repeated excepting that the amount of oleic acid chloride reacted is increased to about 2:1 molar ratio and 3:1 molar ratio compared to 1,3,5-tri(2-hydroxyethyl)perhydro-s-triazine, respectively. The compounds prepared are recovered and identified as 1,3,5-triazine-1,3,5-(2H, 4H, 6H)triethanol dioleate and 1,3,5-triazine-1,3,5-(2H, 4H, 6H)triethanol trioleate.

EXAMPLE 4

Corrosion Testing

A synthetic crude oil is simulated by combining equal volumes of heavy mineral oil and aqueous 2 percent brine solution (containing primarily chloride salts of sodium and calcium). The synthetic crude oil is purged with a nitrogen stream then saturated with carbon dioxide. Hydrogen sulfide is generated in situ at a concentration of 50 ppm by addition of 6.15 ml of glacial acetic acid and sodium sulfide-9-hydrate (1.1 g) to 3 liters of brine.

The inhibitors further identified in Table I are added to the synthetic crude oil to provide an inhibitor concentration of 100 ppm. A sample of the solution (320 ml) is added to a sealable glass bottle containing a mild steel coupon (4.4 g). The bottle is sealed and agitated for 72 hours at 65° C. The weight losses of coupons treated in this manner are compared to those of similar coupons in fluids containing no inhibitor. The percent protection is calculated as percent weight loss/percent weight loss of control × 100. Results are contained in Table I.

TABLE I

| Inhibitor | % Protection |
| --- | --- |
| 1,3,5-triazine-1,3,5-(2H,4H,6H)— triethanol monooleate | 77 |
| 1,3,5-triazine-1,3,5-(2H,4H,6H)— triethanol dioleate | 77 |
| 1,3,5-triazine-1,3,5-(2H,4H,6H)— triethanol trioleate | 72 |
| 1,3,5-tris(2-hydroxyethyl)perhydro-s-triazine (not of the invention) | 11 |

It is seen that the esterified compounds of the present invention exhibited improved corrosion protection compared to unesterified compounds.

What is claimed is:

1. A compound corresponding to the formula:

$$XOCHR_1CH_2N\underset{\underset{CH_2CHR_1OX}{\overset{|}{N}}}{\overbrace{\phantom{XXXXX}}}N{-}CH_2CHR_1OX$$

wherein $R_1$ is hydrogen, methyl or ethyl; and

X is hydrogen, $-CH_2CHR_1O)_nR$ or $-C(O)R$, where n is a number from zero to about 4, and R is alkyl, cycloalkyl, alkenyl or aryl of up to about 30 carbons, provided that in at least on occurence, X is $-C(O)R$.

2. A compound according to claim 1 wherein R is the remnant of saturated or unsaturated fatty acid of from 4 to 30 carbons.

3. A compound according to claim 2 wherein R is a remnant of lauric, nonoic, sebacic, palmitic, stearic, oleic, linoleic, or linolenic acid or a mixture thereof.

4. A compound according to claim 1 wherein R is a remnant of oleic acid.

5. A compound according to claim 4 selected from the group consisting of 1,3,5-triazine-1,3,5-(2H, 4H, 6H)triethanol monooleate, 1,3,5-triazine-1,3,5-(2H, 4H, 6H)triethanol dioleate, and 1,3,5-triazine-1,3,5-(2H, 4H, 6H)triethanol trioleate.

* * * * *